United States Patent [19]
Gellenbeck

[11] Patent Number: 5,976,575
[45] Date of Patent: Nov. 2, 1999

[54] DRY CAROTENOID-OIL POWDER AND PROCESS FOR MAKING SAME

[75] Inventor: Kevin W. Gellenbeck, Poway, Calif.

[73] Assignee: Amway Corporation, Ada, Mich.

[21] Appl. No.: 09/126,564

[22] Filed: Jul. 30, 1998

Related U.S. Application Data

[62] Division of application No. 08/580,385, Dec. 28, 1995, Pat. No. 5,827,539.

[51] Int. Cl.$^6$ ....................................................... A61K 9/14
[52] U.S. Cl. ......................... 424/489; 424/461; 424/464; 424/493; 424/451
[58] Field of Search ..................................... 424/489, 464, 424/488; 588/351

[56] References Cited

U.S. PATENT DOCUMENTS

| | | |
|---|---|---|
| 2,496,634 | 2/1950 | Melnick . |
| 2,686,751 | 7/1954 | Enbree et al. . |
| 2,827,452 | 3/1958 | Schlenk et al. . |
| 2,876,160 | 3/1959 | Schoch et al. . |
| 3,316,101 | 4/1967 | Borenstein et al. . |
| 3,655,406 | 4/1972 | Klaui . |
| 3,666,557 | 5/1972 | Jensen et al. . |
| 3,786,123 | 1/1974 | Katzen . |
| 3,790,688 | 2/1974 | Walter, Jr. et al. . |
| 3,886,294 | 5/1975 | Emodi et al. . |
| 3,962,416 | 6/1976 | Katzen . |
| 3,998,753 | 12/1976 | Antoshkiw et al. . |
| 4,053,646 | 10/1977 | Wright et al. . |
| 4,230,687 | 10/1980 | Sair et al. . |
| 4,276,312 | 6/1981 | Merritt . |
| 4,316,917 | 2/1982 | Antoshkiw et al. . |
| 4,698,264 | 10/1987 | Steinke . |
| 4,911,952 | 3/1990 | Doane et al. . |
| 4,913,915 | 4/1990 | Tanaka . |
| 4,915,961 | 4/1990 | Tanaka . |
| 4,915,965 | 4/1990 | Tanaka . |
| 4,931,467 | 6/1990 | Saint-Leger et al. . |
| 5,023,095 | 6/1991 | Kirk . |
| 5,087,461 | 2/1992 | Levine et al. . |
| 5,290,481 | 3/1994 | Todd . |
| 5,811,609 | 9/1998 | Vilstrup et al. .......................... 585/351 |

*Primary Examiner*—Thurman K. Page
*Assistant Examiner*—William E. Benston
*Attorney, Agent, or Firm*—Warner Norcross & Judd LLP

[57] ABSTRACT

A dry powder that contains carotenoids produced by grinding a mixture of carotenoids and oil to reduce the carotenoid particle size, emulsifying the mixture with an encapsulating mixture, and drying the emulsification. The encapsulating mixture includes a starch encapsulating agent, a sugar, and an anti-oxidant. The resulting water-dispersible powder contains a high concentration of carotenoids, yet is protected from oxidation.

20 Claims, 1 Drawing Sheet

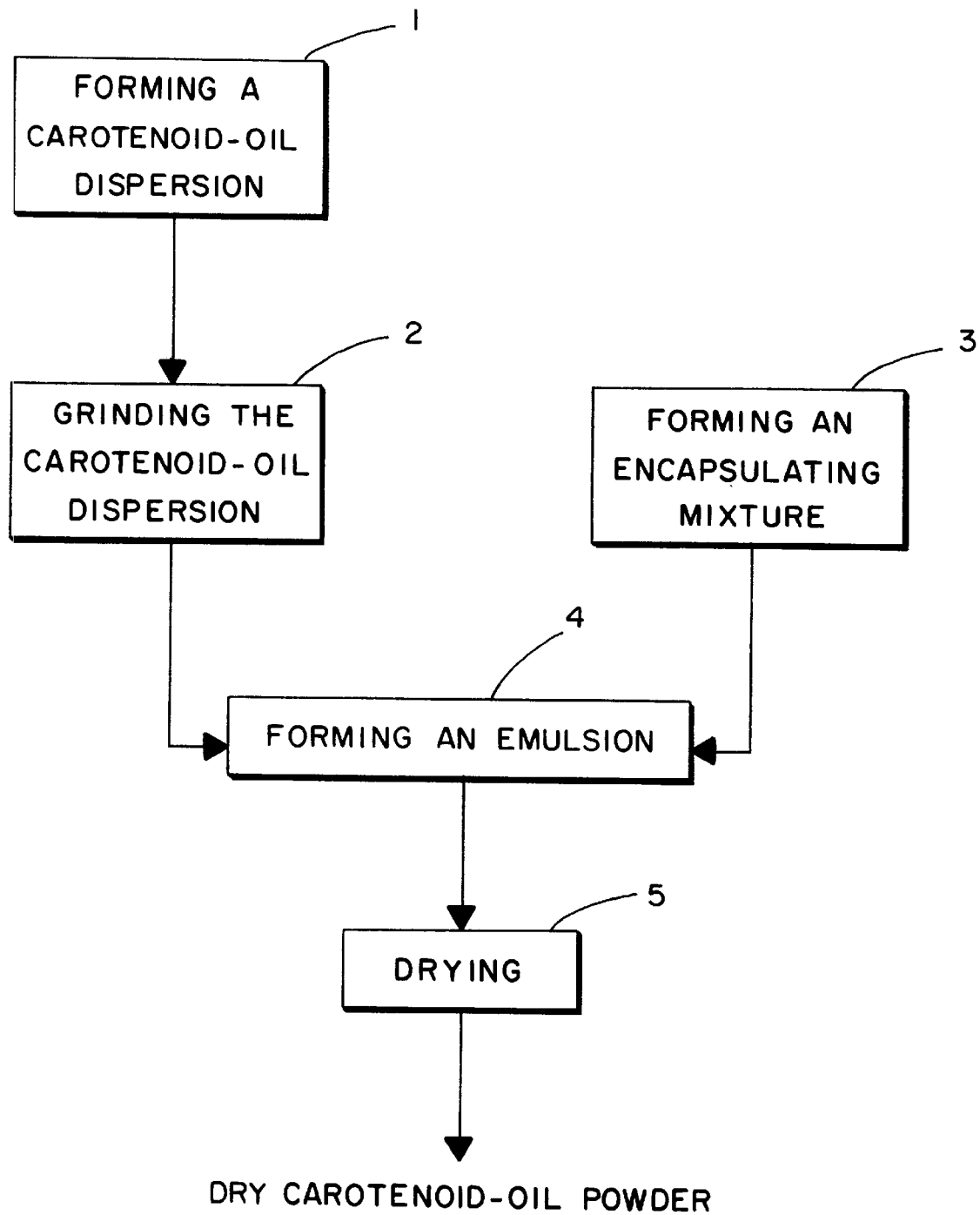
FIG. I

DRY CAROTENOID-OIL POWDER AND PROCESS FOR MAKING SAME

This application is a divisional of Ser. No. 08/580,385 filed Dec. 28, 1995 (now U.S. Pat. No. 5,827,539).

BACKGROUND OF THE INVENTION

The present invention relates to carotenoid compounds, and more particularly to carotenoid-oil dispersions encapsulated within protective starch encasements.

Carotenoids are a class of organic pigments that are often used to provide safe coloration of food. Carotenoids include carotenes (e.g., beta-carotene and lycopene), which are $C_{40}$ carotenoids containing 11 or fewer conjugated carbon-carbon double bonds, and xanthophylls (e.g., lutein and astaxanthin), which are oxygen-containing carotenoids. Carotenoids are moderately soluble in oil and are insoluble in water.

In addition to the use of carotenoids as pigments, some carotenoids also have nutritional value. For example, beta-carotene is widely used as a vitamin A precursor (i.e., provitamin A) since beta-carotene is metabolically oxidized to vitamin A (retinol) in most animals.

One problem associated with carotenoids is their susceptibility to oxidation. For example, beta-carotene will react with oxygen from the air, resulting in an inactive, colorless oxidation product. Thus, over time, a carotenoid that is exposed to air without the protection of encapsulation and/or antioxidants will lose its pigmentation and nutritional attributes.

Carotenoids are often supplied in oil dispersions rather than in crystalline form in order to "stabilize" the carotenoids, that is, reduce the amount of the degradation caused by exposure to oxygen, heat, or light. Further, carotenoids supplied in an oil dispersion are less susceptible to damage from handling during transportation. Additionally, it is believed that carotenoids in an oil dispersion are more readily absorbed or ingested, and thus have better nutritional attributes.

It is known that liquid and solid chemical agents that are "sensitive" (i.e., subject to degradation when exposed to external elements) can be protected by encapsulating them within a dry starch matrix. For example, U.S. Pat. No. 2,876,160 to Schoch et al teaches the protection of agents (e.g., insecticides, flavoring oils, fatty acids, medicinals, and beta-carotene) from physical and chemical deterioration by encapsulating the agent within a starch matrix. In that method, a liquid or solid agent is gradually added with vigorous agitation, which may include agitation by use of a mechanical emulsifier or pressure homogenizer, to an aqueous starch solution, which may contain plasticizers such as glucose syrup. The resulting emulsion or dispersion is dried using methods such as spray-drying. If a solid agent is to be protected, it may be "powdered" prior to adding it to the starch solution.

Other examples of starch encapsulation of sensitive agents are disclosed in U.S. Pat. No. 4,276,312 to Merritt (teaching the protection of vitamins and flavor agents from oxidation or sunlight deterioration by spray-drying a mixture of the agent and starch mixture to form rod-like particles) and U.S. Pat. No. 2,827,452 to Schlenk et al (teaching the use of a starch matrix to protect an agent such as vitamin A acetate from oxidation).

Several variations of the dry starch-coating method have been used to protect sensitive agents, such as flavorings, oils, and vitamins, from sunlight and oxygen. For example, a starch/agent mixture can be partially dried and then ground into a powder (U.S. Pat. Nos. 4,230,687 to Sair et al and 4,911,952 to Doane et al), or the starch/agent mixture can be quenched in oil and then dehydrated to form beadlets (U.S. Pat. No. 3,666,557 to Jensen et al).

While it is important to encapsulate a carotenoid dispersion with a sufficient amount of coating to protect the carotenoids from degradation, it is advantageous to minimize the amount of coating relative to the amount of carotenoid in order to minimize the amount of inactive ingredients that merely add to the bulk of a product containing the encapsulated carotenoid-oil dispersion. For example, if a dry-powder carotenoid dispersion is to be used in a tablet, a bulky coating of unnecessary ingredients can interfere with the tableting process. If the dry-powder carotenoid is to be used in a powdered drink mix, a bulky coating of unnecessary ingredients can needlessly increase the volume and weight of the drink mix. Thus, it is preferable to maximize the "potency" (i.e., the concentration of carotenoid) of the encapsulated carotenoid-oil dispersion in order to limit the amount of inactive ingredients.

The art discloses methods of increasing the stability of dry-powder carotenoid products. However, the potency of the carotenoid products is relatively low; and stability is achieved by utilizing synthetic (i.e., not produced by nature) ingredients.

SUMMARY OF THE INVENTION

The aforementioned problems are overcome in the present invention comprising a process for making a dry carotenoid-oil powder that is both stable and highly potent. More specifically, an oil dispersion containing carotenoid particles is ground or milled so that the average diameter of the undissolved carotenoid particles within the dispersion are less than about one micron. An encapsulating mixture is formed by dissolving a starch encapsulating agent, a sugar, and an antioxidant in water. The milled carotenoid-oil dispersion is then emulsified with the encapsulating mixture. Finally, the resulting emulsion is dried to produce a powder having the carotenoid-oil dispersion encapsulated within a protective starch matrix.

The water-dispersible, dry carotenoid-oil powders produced by the process of the present invention have high potencies while maintaining good resistance to oxidation. Further, the powders can be produced utilizing only natural ingredients.

These and other objects, advantages, and features of the invention will be more readily understood and appreciated by reference to the detailed description of the preferred embodiment.

BRIEF DESCRIPTION OF THE DRAWING

FIG. 1 is a flow chart illustrating the method steps of the present invention.

DETAILED DESCRIPTION OF THE PREFERRED EMBODIMENT

The present invention is a method of producing a high-potency, water-dispersible, dry carotenoid-oil powder that resists degradation caused by exposure to oxygen. Referring to FIG. 1, the high potency (i.e., concentration) of carotenoid in the final product requires the step 1 of forming a carotenoid-oil dispersion and the step 2 of grinding or milling the carotenoid-oil dispersion to reduce the size of the carotenoid particles. Protection of the carotenoid particles from oxidation requires the step 3 of preparing an encapsulating mixture, the step 4 of emulsifying the ground carotenoid-oil dispersion within the encapsulating mixture, and the step 5 of drying the resulting emulsion mixture. Consequently, the carotenoid particles within the oil droplets are encased within a protective, water-soluble coating.

Carotenoid-Oil Dispersion

Turning to FIG. 1 step 1, to produce a high-potency product, it is advantageous to use as a raw material feedstock a carotenoid-oil dispersion (i.e., a crystalline slurry) that contains a high percentage of carotenoid. If a product manufactured from only natural ingredients is desired (as in the present invention), then the carotenoid-oil dispersion must contain natural components, that is, components found in or produced by living things. One suitable carotenoid-oil dispersion that contains only natural ingredients is that sold under the trademark PROVATENE®, which is a beta-carotene in oil mixture manufactured by the Nutrilite Division of Amway Corporation and available in concentrations of up to 3.5 percent beta-carotene. The PROVATENE® product is a vegetable extract of Dunaliella algae, vitamin E, and beta-carotene. Other similar carotenoid-oil dispersions are available from Betatene Ltd., a subsidiary of Henkel, Inc., and Western Biotechnology Ltd., an Australian company. Other natural carotenoid-oil dispersions are available, as is known in the art.

Preferably, the carotenoid-oil dispersion is further concentrated to increase the percentage of carotenoids. For example, the PROVATENE® product is centrifuged to concentrate the beta-carotene crystals in one portion of the oil-dispersion to about 5 percent beta-carotene. A preferred concentrated carotenoid-oil dispersion is sold under the trademark PROVATENOL™ by Koyo Mercantile of Japan. This dispersion is concentrated PROVATENE® product, produced using a solvent extraction process. The PROVATENOL™ product contains about 30 weight percent beta-carotene in oil.

Turning to FIG. 1 step 2, the carotenoid crystals present in the carotenoid-oil dispersion are ground to reduce the size of these particles, and to produce a milled carotenoid-oil dispersion. The carotenoid particles in the milled carotenoid-oil dispersion must be small enough to fit within the approximately one micron average diameter oil droplets that form in an emulsion of the milled carotenoid-oil dispersion and the encapsulating mixture (discussed below). To reduce the size of the carotenoid particles within the carotenoid-oil dispersion to below about one micron average diameter, the mixture is ground, preferably using a ball mill. Generally, it is easier to achieve the small particle size needed for the present invention by grinding concentrated carotenoid-oil dispersions, because a higher particle population enhances the grinding effects and thus reduces the number of large particles. A suitable ball mill is model number LMJ 05 sold by Netzsch, Inc. Preferably, the amount of time between milling the carotenoid-oil dispersion and using the milled mixture as a component for the present invention is minimized to avoid recrystallization (i.e., reforming into larger particles) of the carotenoid particles.

II. Encapsulating Mixture

Referring to FIG. 1 step 3, an encapsulating mixture is formed by mixing a starch encapsulating agent, a sugar, and an antioxidant in water. The starch encapsulating agent is a starch or starch/additive mixture suitable to encapsulate flavors, fats, oils, or vitamins, as is known in the art. Preferably, the starch encapsulating agent is a modified food starch encapsulating agent. Several suppliers have proprietary formulations for their commercially available modified food starch encapsulating agents. One such modified food starch encapsulating agent found to be suitable in the present invention as an encapsulating agent is N-LOK® starch encapsulating agent, available from National Starch and Chemical Corporation. Generally, N-LOK® starch encapsulating agent is a modified food starch with corn syrup solids added. The encapsulating mixture should contain at most about 91 weight percent starch encapsulating agent on a dry basis, and preferably at most about 84 weight percent starch encapsulating agent on a dry basis.

The sugar used in the encapsulating mixture is a sugar suitable to contribute to the solubility of the encapsulating coating when the carotenoid-oil powder is exposed to water, as is known in the art. It is believed that the sugar contributes to the formation of an encapsulating coating by forming a glass-like crystalline structure providing good oxidative protection. Suitable sugars are sucrose and fructose. Other sugars known in the art are also suitable. The encapsulating mixture should contain at least about 5 weight percent sugar on a dry basis, and preferably at least about 10 weight percent sugar on a dry basis.

The antioxidant used in the encapsulating mixture is a food-grade antioxidant suitable to protect carotenoids from degradation, while surviving the processing conditions of the present invention, as is known in the art. If a final product manufactured from only natural ingredients is desired, then only natural antioxidants are used. The presently preferred antioxidant is sodium ascorbate and vitamin E acetate. Preferably, vitamin E acetate is used in combination with the sodium ascorbate; however, some countries do not permit vitamin E acetate as a food additive.

In order to reduce the cost of the final dry powder, it is desirable to reduce the antioxidant to the amount necessary to maintain good stability (i.e., oxidation resistance) in the final dry product. The encapsulating mixture should contain at least about 4 weight percent antioxidant on a dry basis, and preferably at least about 6 weight percent antioxidant on a dry basis.

The starch encapsulating agent, sugar, and antioxidants are dissolved in water, preferably deionized water, to form the encapsulating mixture. Preferably, the encapsulating mixture contains about 40 weight percent total solids and about 60 weight percent water. Also preferably, the sugar is dissolved in the water prior to dissolving the other ingredients.

III. Emulsion and Drying

Referring to FIG. 1 step 4, after preparation of the milled carotenoid-oil dispersion and the encapsulating mixture, these two components are blended to form a coarse emulsion. To increase the potency of the final product, the ratio of encapsulating mixture to milled carotenoid-oil dispersion preferably is reduced when forming the coarse emulsion to the point at which the stability of the final product becomes unacceptable. A final product having good stability is produced when the coarse emulsion has a weight ratio of the total solids of the encapsulating mixture to the total solids of the milled carotenoid-oil dispersion of about 4-to-1. A coarse emulsion having a ratio of 3-to-1 produces a final dry powder having more surface oil than a product made using a 4-to-1 ratio. The additional surface oil causes the final dry product to be sticky, and thus to clump or to stick to the sides of a container. Further, this stickiness causes problems during the drying step of the process of this invention. A coarse emulsion having a ratio of 2-to-1 produces a final product with poor stability. Therefore, the ratio of about 4-to-1 is preferred.

The coarse emulsion is then further emulsified by using emulsifying or homogenizing equipment known in the art. The coarse emulsion should be emulsified to produce a visually stable emulsion, preferably without any free-floating carotenoid crystals. Preferably, a high-pressure emulsifier or homogenizer is used. A suitable emulsifier for the method of the present invention is a model number M-110F or M210 Microfluidizer high-pressure homogenizer available from Microfluidics. The coarse emulsion is passed through the high-pressure emulsifier at a pressure of between 11,000 to 12,000 p.s.i.g.

Referring to FIG. 1 step 5, the emulsion is dried to produce a powder, using techniques that are known in the art. Preferably, the emulsion is spray-dried. Care should be taken so that the carotenoids within the emulsion are not degraded by excess heat.

It is believed that one reason the dry carotenoid-oil powder produced using the method of the present invention has high potency, while retaining good resistance to oxidation, is because the carotenoid particles are ground small enough to be suspended (i.e., "fit") within the tiny oil droplets formed during the emulsification step. Once the oil droplets are dispersed throughout the encapsulating mixture by emulsification, and the resulting emulsion is dried, the oil droplets, and thus the suspended carotenoid particles, are encased within a protective coating.

Regardless of the actual chemical mechanism, the dry, water-dispersible carotenoid-oil powders formed using the method of the present invention have high potencies (i.e., carotenoid concentrations), while maintaining good resistance to oxidation. Further, the resistance to oxidative degradation can be achieved in a final product containing only natural ingredients. While the discussion of the present invention has been directed to carotenoids, it is believed that the process would be useful to increase the potency of other compounds that can be dispersed within an oil, and whose stability is enhanced by a protective starch encasement.

The following examples are presented for the purpose of further illustrating and explaining the present invention and are not to be taken as limiting in any regard. Unless otherwise indicated, all parts and percentages are by weight.

EXAMPLE I

A one kilogram sample of the PROVATENOL product (30 percent beta-carotene-oil dispersion from Koyo Mercantile in Japan, assayed at about 25 percent beta-carotene) was ball-milled utilizing a Netzsch ball mill model number LMJ O5, under the following operating conditions:

Recirculation Time: 90 minutes
Grinding Media: 0.6 mm Yttrium Stabilized Zirconium Oxide
Media Charge: 90% of chamber volume
Agitator Speed: 2650 RPM
Residence Time: 29 minutes The milling produced beta-carotene particles with the attributes shown in Table I.

TABLE I

| Percentage of Particles | Diameter (microns) |
| --- | --- |
| 99 | less than 1.61 |
| 50 | less than 0.50 |
| Mean Volume Diameter | 0.57 |

An encapsulating mixture was formed by mixing the following components in the amount noted: 33.6 percent N-LOK® starch encapsulating agent, 4 percent fructose, 1.6 percent sodium ascorbate, 0.8 percent vitamin E acetate (50 percent strength), and 60 percent deionized water. (On a dry basis, these percentages are 84 percent N-LOK® starch encapsulating agent, 10 percent fructose, 4 percent sodium ascorbate, and 2 percent vitamin E acetate (50 percent strength).) After these components were dissolved to form the encapsulating mixture, an amount of the milled PROVATENOL product was added to the encapsulating mixture so that ratio of the weight of the total solids of the encapsulating mixture to the total solids of the milled PROVATENOL product was about 4-to-1. This mixture was shaken to form a coarse emulsion. The coarse emulsion was then further emulsified by running the coarse emulsion through two passes in an M-110F Microfluidizer available from Microfluidics, operating at a pressure of 12,000 p.s.i.g. The emulsion appeared visually stable; any beta-carotene particles visible before the high-pressure emulsification disappeared after the processing.

The emulsion was then dried using an APV Pilot Spray Dryer. The inlet temperature was 302° F., which when stabilized, produced an exit temperature of about 235° F. The run produced a dry-powder that was assayed as having a potency (i.e., beta-carotene content) of 4.4 percent.

The stability of the dry-powder product was tested by tightly sealing the powder in a plastic jar, and placing the jar in a chamber maintained at 38.5° C. and 75 percent relative humidity for 13 weeks. At the end of this period, the potency of the product was 3.5 percent, which is about 80 percent of the original potency. Thirteen weeks under the conditions of this test are believed to roughly predict the stability performance of a carotenoid dry-powder formulation in two years at room temperature.

EXAMPLE II

A one kilogram sample of Lyc-O-Pen product (5 percent lycopene oleoresin manufactured by LycoRed Natural Products Industries, Ltd. in Israel) was ball-milled utilizing a Netzsch ball mill model number LMJ O5, under the following operating conditions:

Recirculation Time: 60 minutes
Grinding Media: 0.4 mm Yttrium Stabilized Zirconium Oxide
Media Charge: 90% of chamber volume
Agitator Speed: 2600 RPM
Residence Time: 23 Minutes Microscopic examination showed the milled lycopene-oil dispersion with most particles having a diameter of about one micron, and with very few particles having a diameter larger than 2 to 3 microns.

An encapsulating mixture was formed using 33.6 percent N-LOK® starch encapsulating agent, 4 percent fructose, 1.6 percent sodium ascorbate, 0.8 percent vitamin E acetate (50 percent strength), and 60 percent deionized water. (On a dry basis, these percentages are 84 percent N-LOK® starch encapsulating agent, 10 percent fructose, 4 percent sodium ascorbate, and 2 percent vitamin E acetate (50 percent strength).) After these components were dissolved to form the encapsulating mixture, an amount of milled Lyc-O-Pen was added to the encapsulating mixture so that ratio of the weight of the total solids of the encapsulating mixture to the total solids of the milled Lyc-O-Pen was about 4-to-1. This mixture was shaken to form a coarse emulsion. The coarse emulsion was then further emulsified by running the coarse emulsion through two passes in an M-110F Microfluidizer available from Microfluidics, operating at a pressure of 11,000 p.s.i.g.

The emulsion was then dried on an APV Pilot Spray Dryer. The inlet temperature was 304° F., which when stabilized, produced an exit temperature of about 234° F., for a flow rate of 30 to 32 milliliters/minute. The run produced a dry-powder that was assayed as having a lycopene content of about 0.90 percent.

The stability of the dry-powder product was tested by placing the powder in open test tubes, and placing the test tubes in a forced air oven at a temperature of 55° C. for 14 days. At the end of this period, the potency of the product was 0.73 percent, about 81 percent of the original potency. Fourteen days under the conditions of this test are believed to roughly predict the stability performance of a carotenoid dry-powder formulation in the 13-week testing conditions described in Example I.

EXAMPLE III

Beta-carotene crystals were mixed into a PROVATENE® carotenoid-oil dispersion having 2.15 percent beta-carotene, to produce a PROVATENE® mixture containing 2.55 percent beta-carotene. This mixture was ball-milled utilizing a Netzsch ball mill model number LMJ O5, under the following operating conditions:

Recirculation Time: 120 minutes
Grinding Media: 0.6 mm Yttrium Stabilized Zirconium Oxide
Media Charge: 90% of chamber volume
Agitator Speed: 2800 RPM
Residence Time: 13.5 minutes The milling produced beta-carotene particles with the attributes shown in Table II.

TABLE II

| Percentage of Particles | Diameter (microns) |
|---|---|
| 99 | less than 0.43 |
| 50 | less than 0.26 |
| Mean Volume Diameter | 0.27 |

Two encapsulating mixtures were formed. Encapsulating Mixture A contained 86 percent N-LOK® starch encapsulating agent, 10 percent fructose, and 4 percent sodium ascorbate, calculated on a dry basis. Encapsulating Mixture B contained 84 percent N-LOK® starch encapsulating agent, 10 percent fructose, 4 percent sodium ascorbate, and 2 percent vitamin E acetate (50 percent strength), calculated on a dry basis. Water was added to achieve a final level of 40 percent solids. When dissolving these components in water to form Encapsulating Mixtures A and B, the sugar was dissolved in the water first. An amount of milled PROVATENE carotenoid-oil dispersion was added to both Encapsulating Mixture A and B so that the ratio of the weight of the total solids of the encapsulating mixture to the total solids of the milled PROVATENE carotenoid-oil dispersion was about 4-to-1. These mixtures were shaken to form a coarse emulsion, and then passed through a French Press (SLM Instruments French Pressure Cell, Model FA078) maintaining 10,000 to 11,000 p.s.i.g. to make Final Emulsions A and B. Emulsions A and B were then dried using a Buchi 190 Mini Spray Dryer. The inlet temperature was 308° F., the exit temperature was 226° F., and the sample flow rate was 4 milliliters per minute. The run produced "A" and "B" dry powders that were both assayed as having a beta-carotene content of about 0.5 percent.

The stability of the A and B dry powders was tested by placing the powders in open test tubes, and placing the test tubes in a forced air oven at a temperature of 55° C. for 15 days. At the end of this period, the potency of the A dry powder was about 84 percent of its original potency, and the potency of the B dry powder was about 88 percent of its original potency.

The above descriptions are those of preferred embodiments of the invention. Various alterations and changes can be made without departing from the spirit and broader aspects of the invention as defined in the claims, which are to be interpreted in accordance with the principles of patent law, including the doctrine of equivalents.

The embodiments of the invention in which an exclusive property or privilege is claimed are defined as follows:

1. A dry, powder form of a carotenoid produced by the steps comprising:
   dispersing a carotenoid in an oil to make a carotenoid-oil dispersion;
   grinding the carotenoid-oil dispersion to produce a milled carotenoid-oil dispersion;
   dissolving a starch encapsulating agent, a sugar, and an antioxidant in water to form an encapsulating mixture;
   blending the milled carotenoid-oil dispersion and the encapsulating mixture to form an emulsion; and
   drying the emulsion to produce a powder, whereby the encapsulating mixture encases the milled carotenoid-oil dispersion.

2. A dry, powder form of a carotenoid composition comprising:
   a carotenoid-oil dispersion droplets having carotenoid particles with an average diameter of less than about one micron; and
   an encapsulating coating encasing the droplets, the coating including a starch encapsulating agent, a sugar, and antioxidant.

3. The composition of claim 2 wherein the starch encapsulating agent is a modified food starch encapsulating agent.

4. The composition of claim 2 wherein the composition contains at least about 4.4 weight percent carotenoid.

5. The composition of claims 2 wherein the composition consists essentially of components selected from the group consisting of components found in living organisms and components produced by living organisms.

6. The composition of claim 2 wherein the carotenoid-oil dispersion droplets contains carotenoid particles having an average diameter of less than about 0.6 micron, and wherein 99 percent of the carotenoid particles have diameters less than about 1.6 microns.

7. The dry, powder form of a carotenoid of claim 1 wherein said grinding step includes grinding the carotenoid to an average diameter of less than about one micron.

8. The dry, powder form of a carotenoid of claim 1 wherein:
   the carotenoid particles have an average diameter of less than about 0.6 micron; and
   99 weight percent of the carotenoid particles have diameters less than about 1.6 microns.

9. The dry, powder form of a carotenoid of claim 1 wherein the powder contains at least about 4.4 weight percent carotenoid.

10. The dry, powder form of a carotenoid of claim 1 wherein the carotenoid is selected from the group consisting of beta-carotene and lycopene.

11. The dry, powder form of a carotenoid of claim 1 wherein the blending step includes using a high-pressure homogenizr to create the emulsion.

12. The dry, powder form of a carotenoid of claim 1 wherein the grinding step includes using a ball mill.

13. The dry, powder form of a carotenoid of claim 11 wherein the starch encapsulating agent is a modified food starch encapsulating agent.

14. The dry, powder form of a carotenoid of claim 1 wherein the encapsulating mixture contains at least about 5 weight percent sugar on a dry basis.

15. The dry, powder form of a carotenoid of claim 1 wherein the carotenoid-oil dispersion contains only natural components.

16. The dry, powder form of a carotenoid of claim 1 wherein the antioxidant consists essentially of one or more components found in or produced by living organisms, or mixtures thereof.

17. The dry, powder form of a carotenoid of claim 1 wherein the encapsulating a mixture contains at least about 4 weight percent antioxidant on a dry basis.

18. The dry, powder form of a carotenoid of claim 1 wherein the encapsulating mixture comprises about 40 weight percent solids and about 60 weight percent water.

19. The dry, powder form of a carotenoid of claim 11 wherein the encapsulating mixture comprises about 84 weight percent modified food starch encapsulating agent, about 10 weight percent sugar, and about 6 weight percent antioxidant, calculated on a dry basis.

20. The dry, powder form of a carotenoid of claim 1 wherein the emulsion comprises total solids from the encapsulating mixture and total solids from the milled carotenoid-oil mixture in a maximum weight ratio of about 4-to-1.

* * * * *

UNITED STATES PATENT AND TRADEMARK OFFICE
CERTIFICATE OF CORRECTION

PATENT NO. : 5,976,575
DATED : November 2, 1999
INVENTOR(S) : Gellenbeck

It is certified that error appears in the above-identified patent and that said Letters Patent is hereby corrected as shown below:

Column 9, Claim 13, Line 1:
  claim "11" should be --1--

Column 9, Claim 17, Line 15:
  after "encapsulating" delete --a--

Column 10, Claim 19, Line 4:
  claim "11" should be --1--

Signed and Sealed this

Fifteenth Day of August, 2000

Attest:

Q. TODD DICKINSON

*Attesting Officer*  *Director of Patents and Trademarks*